United States Patent

Breuer et al.

[11] 4,028,354
[45] June 7, 1977

[54] ALKENYL AND ALKINYLUREIDO CEPHALOSPORINS

[75] Inventors: Hermann Breuer; Uwe D. Treuner, both of Regensburg, Germany

[73] Assignee: E. R. Squibb & Sons, Inc., Princeton, N.J.

[22] Filed: Mar. 8, 1976

[21] Appl. No.: 664,467

[52] U.S. Cl. .................. 260/243 C; 260/332.2 A; 424/246
[51] Int. Cl.² ...................................... C07D 501/36
[58] Field of Search ............................... 260/243 C

[56] References Cited

UNITED STATES PATENTS

| | | | |
|---|---|---|---|
| 3,673,183 | 6/1972 | Erickson | 260/243 C |
| 3,687,641 | 8/1972 | Holdrege | 260/243 C |
| 3,708,479 | 1/1973 | Welch et al. | 260/243 C |
| 3,775,410 | 11/1973 | Christensen et al. | 260/243 C |
| 3,780,031 | 12/1973 | Christensen et al. | 260/243 C |
| 3,780,033 | 12/1973 | Hazen | 260/243 C |
| 3,780,034 | 12/1973 | Christensen et al. | 260/243 C |
| 3,833,568 | 9/1974 | Dolfini et al. | 260/243 C |
| 3,843,641 | 10/1974 | Christensen et al. | 260/243 C |
| 3,860,591 | 1/1975 | Breuer | 260/243 C |
| 3,925,368 | 12/1975 | Cooper et al. | 260/243 C |
| 3,954,802 | 5/1976 | Kocsis | 260/243 C |
| 3,956,292 | 5/1976 | Cooper | 260/243 C |
| 3,978,051 | 8/1976 | Dolfini | 260/243 |

Primary Examiner—Donald G. Daus
Assistant Examiner—D. E. Wheeler
Attorney, Agent, or Firm—Lawrence S. Levinson; Merle J. Smith; Stephen B. Davis

[57] ABSTRACT

Alkenyl and alkinylureido cephalosporins of the formula

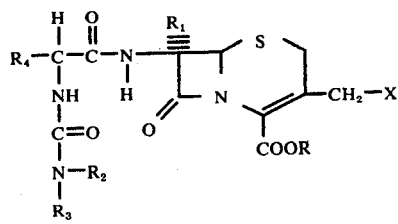

wherein R is hydrogen, lower alkyl, phenyl-lower alkyl, diphenyl-lower alkyl, tri(lower alkyl)silyl, trihaloethyl, a salt forming ion, or the group

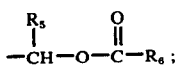

$R_1$ is hydrogen or methoxy; $R_2$ is lower alkenyl or lower alkinyl, $R_3$ is hydrogen or lower alkyl; $R_4$ is hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups; $R_5$ is hydrogen or lower alkyl; $R_6$ is lower alkyl; and X is hydrogen, lower alkanoyloxy,

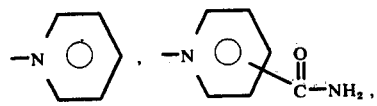

or certain heterothio groups; are disclosed. These compounds are useful as antibacterial agents.

35 Claims, No Drawings

ALKENYL AND ALKINYLUREIDO CEPHALOSPORINS

BACKGROUND OF THE INVENTION

Cephalosporins having a ureido acyl side chain are disclosed in U.S. Pat. Nos. 3,673,183; 3,708,479; 3,833,568; and 3,860,591. Cephalosporins having various acyl side chains and a 7α-methoxy substituent are taught in various U.S. patents including U.S. Pat. Nos. 3,775,410; 3,780,031; 3,780,033; 3,780,034; 3,780,037; 3,843,641; etc.

Cephalosporins having an acylureido acyl side chain are disclosed in U.S. Pat. Nos. 3,687,949 and 3,925,368 and German Offenlegungsschrift Nos. 2,513,954 and 2,514,019.

SUMMARY OF THE INVENTION

This invention relates to new alkenyl and alkinylureido- 7α-methoxy or desmethoxy cephalosporin derivatives of the formula

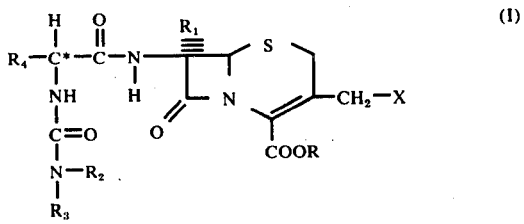

R represents hydrogen, lower alkyl, phenyl-lower alkyl, diphenyl-lower alkyl, tri(lower alkyl) silyl, trihaloethyl, a salt forming ion, or the group

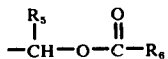

wherein $R_5$ is hydrogen or lower alkyl and $R_6$ is lower alkyl.

$R_1$ represents hydrogen or methoxy. The $R_1$ substituent is in the α-configuration as indicated by the broken lines ($\equiv$).

$R_2$ represents lower alkenyl or lower alkinyl.

$R_3$ represents hydrogen or lower alkyl.

$R_4$ represents hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups.

X represents hydrogen, lower alkanoyloxy, certain heterothio groups,

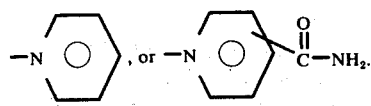

When X is pyridinium or carbamoyl substituted pyridinium, the compounds can be structurally represented as having the formula

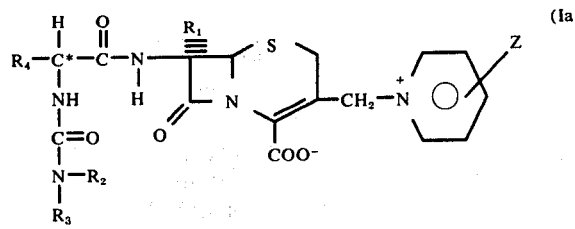

wherein Z is hydrogen or carbamoyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, t-butyl, etc. The lower alkoxy groups include such lower alkyl groups attached to an oxygen, e.g., methoxy, ethoxy, propoxy, etc. The phenyl-lower alkyl and diphenyl-lower alkyl groups include such lower alkyl groups attached to a phenyl, preferably benzyl, phenethyl, and diphenylmethyl.

The lower alkenyl and lower alkinyl groups referred to throughout this specification include straight or branched chain hydrocarbon groups containing 2 to 8 carbon atoms and one double or triple bond, preferably 2 to 4 carbons. Examples of the types of group contemplated are $-CH_2-CH=CH_2$, $-CH=CH_2$, $-CH_2-CH=CH-CH_3$,

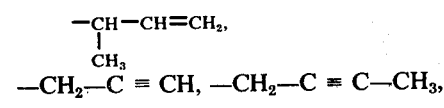

$-CH_2-C\equiv CH$, $-CH_2-C\equiv C-CH_3$,

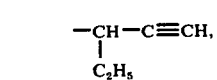

etc.

Cycloalkyl refers to groups having 3 to 7 carbons in the ring, i.e. cyclopropyl, cyclobutyl, cyclopentyl, cyclohexyl, and cycloheptyl. The term cycloalkenyl also represent rings having 3 to 7 carbons with one double bond, i.e. cyclobutenyl, cyclopentenyl, cyclohexenyl, etc. The term cycloalkadienyl represents a ring having 6 or 7 carbons with two double bonds located at various positions such as 1,4-cyclohexadienyl which is preferred.

The substituted phenyl and substituted phenyl-lower alkyl groups include one or two substituents selected from halogen (preferably chlorine or bromine), lower alkyl of 1 to 4 carbons (preferably methyl or ethyl), lower alkoxy of 1 to 4 carbons (preferably methoxy or ethoxy), and hydroxy, e.g. 2-, 3-, or 4-chlorophenyl, 2-, 3-, or 4-bromobenzyl, 2-, 3-, or 4-hydroxyphenyl, 3,5-dichlorophenyl, 2-, 3-, or 4- methylphenyl, 2-, 3-, or 4-ethoxyphenyl, etc.

The salt forming ions represented by R may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N- lower alkylpiperidines such as N-ethylpiperidine. Sodium and potassium are the preferred salt forming ions.

The halogens are the four common halogens, of which chlorine and bromine are preferred. In the case of the trihaloethyl group represented by R,2,2,2-trichloroethyl is preferred.

Trimethylsilyl is the preferred tri(lower alkyl) silyl group.

The heterocyclic groups represented by $R_4$ are 2-thienyl, 3-thienyl, 2-furyl, 3-furyl, 2-pyridyl, 3-pyridyl, or 4-pyridyl. Also included within the meaning of $R_4$ are such heterocyclics having a halogen (preferably Cl or Br) or a lower alkyl of 1-4 carbons (preferably methyl or ethyl) substituent, i.e. 2-(4-chlorothienly), 3-(4-methylthienyl), etc.

Lower alkanoyloxy refers to a group of the fromula

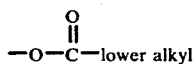

wherein lower alkyl is of 1 to 4 carbons, preferably wherein lower alkyl is methyl.

The hetorothio groups represented by X are

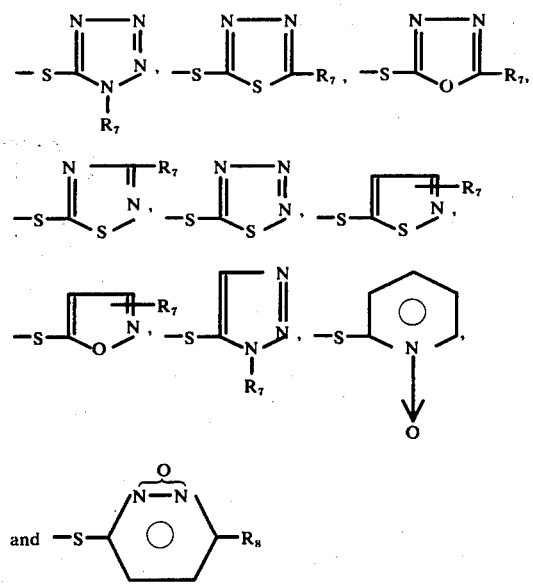

wherein $R_7$ is hydrogen or lower alkyl of 1 to 4 carbons (preferably methyl or ehtyl) and $R_8$ is hydrogen, lower alkyl of 1 to 4 carbons (preferably methyl or ethyl), methoxy, hydroxy, or halogen (preferably chlorine).

The desmethoxy compounds of formula I ($R_1$ is hydrogen) can be prepared by several methods. For example, an α-amino intermediate of the formula

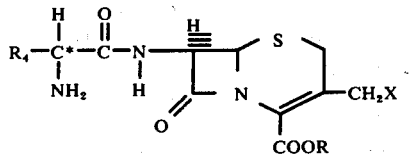

wherein X is hydrogen, lower alkanoyloxy, or heterothio can be reacted, preferably in the form of its trifluoracetic acid salt, with a compound of the formula

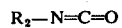

(III)

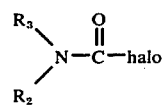

(IV)

or

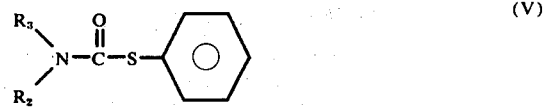

(V)

wherein $R_2$ and $R_3$ are as defined above and halo is Cl or Br to yield the compounds of formula I wherein $R_1$ is hydrogen and X is hydrogen, lower alkanolyloxy, or heterothio.

The α-amino intermediate of formula II can be prepared by various methods such as by acylating a 7-amino cephalosporin of the formula

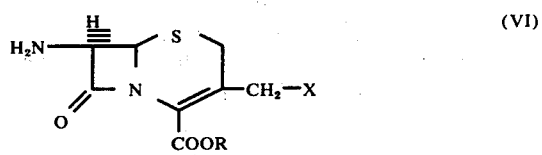

with a substituted α-amino acid of the formula

wherein Y is a protecting group such as

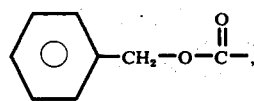

or 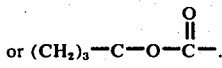.

The α-amino protecting group is then removed by treating the resulting cephalosporin with trifluoroacetic acid and anisole. The α-amino compounds of formula II are taught in various U.S. patents as for example, U.S. Pat. Nos. 3,485,819; 3,507,861; 3,641,021; 3,796,801; 3,813,388; 3,821,207; etc.

Similarly, the 7α-methoxy compounds of fromula I ($R_1$ is methoxy) wherein X is hydrogen, lower alkanoyloxy, or heterothio can be prepared by reacting an α-amino intermediate of the formula

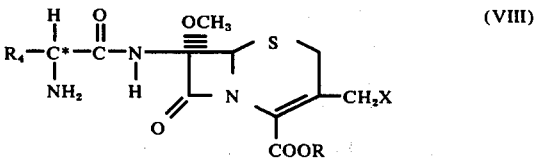

preferably in the form of its trifluoroacetic acid salt with a compound of formula III, IV, or V.

The 7α-methoxy intermediate of formula VIII can be prepared in an analogous manner to the compound of formula II, i.e. by acylating a 7α-methyl-7β-aminocephalosporin of the formula

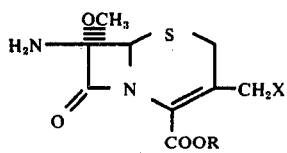
(IX)

with a substituted α-amino acid of formula VII followed by removal of the protecting group. The compounds of formula IX are taught in U.S. Pat. No. 3,897,424 and the preparation of the compound of formula VIII by various other methods are taught in U.S. Pat. Nos. 3,775,410; 3,780,031; 3,780,033; 3,780,034; 3,780,037; 3,887,549; etc.

The compound of formula I wherein $R_1$ is either hydrogen or methoxy and X is pyridinium or carbamoyl substituted pyridinium are prepared by reacting the compound of the formula

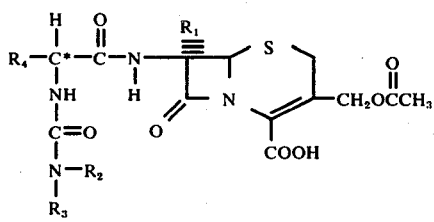
(Ib)

with pyridine or carbamoyl substituted pyridine in a polar solvent such as water and in the presence of a catalyst such as an alkali metal thiocyanate. U.S. Pat. No. 3,792,047 and German Offenlegungsschrift No. 2,234,280 both disclose methods for reacting a cephalosporin so as to replace an acetoxy group with a pyridinium group.

Also, the compounds of formula I wherein $R_1$ is either hydrogen or methoxy and X is heterothio can be prepared by reacting the compound of formula Ib with a mercaptan of the formula

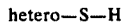
hetero—S—H     (X)

or an alkali metal (preferably sodium) mercaptan salt of the formula

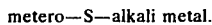
metero—S—alkali metal.     (XI)

Methods for displacing the acetoxy group of a cephalosporin by a heterothio group are taught in various U.S. patents including U.S. Pat. Nos. 3,855,213; 3,890,309; 3,892,737; etc.

The compounds of formula I wherein X is hydrogen, lower alkanoyloxy, or heterothio can also be prepared by reacting a compound of the formula

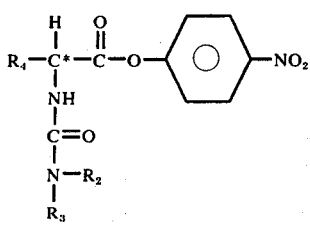
(XII)

with an ester, preferably R is diphenylmethyl, of the compound of formula VI or IX in the presence of hydroxybenzotriazole. The resulting ester is then treated according to methods known in the art to yield the corresponding compound of formula I wherein R is hydrogen.

The compound of formula XII can be prepared by reacting the isocyanatoacetic acid ester of the formula

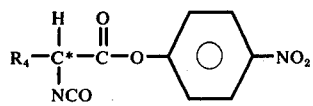
(XIII)

with the compound of the formula

(XIV)

The compounds of formula I wherein R is lower alkyl, phenyl-lower alkyl, trihaloethyl, diphenyl-lower alkyl, or the acyloxymethyl group

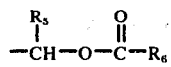

may be obtained by reacting the 7-amino cephalosporin of formula VI or IX either before or after the acylation of the 7-amino substituent with one or two moles of a compound of the formula

halo—R     (XV)

or

$R=N^+=N^-$     (XVI)

wherein halo is preferably chlorine or bromine in an inert solvent such as dimethylformamide, acetone, dioxane, benzene, or the like at about ambient temperature or below.

Similarly, the compounds of formula I wherein R is tri(lower alkyl) silyl are obtained by introducing such groups onto the cephalosporanic acid moiety either before or after the acylation reaction.

The caboxylate salts of the compound of formula I are formed by reacting the carboxyl group of the cephalosporanic acid moiety, i.e. R is hydrogen, with any of the salt forming ions described above.

It will be appreciated that the compounds of formula I are optically active due to the presence of an asymmetric carbon atom represented as C* in the preceding formulas. By selection of the appropriate starting material it is possible to obtain the compounds of formula I as a mixture of optically active isomers or isolated as a single isomer. The various isomers as well as their mixtures are within the scope of this invention.

Preferred compounds of this invention are the acids and alkali metal salts of formula I (i.e. R is hydrogen, sodium, or potassium) wherein X is pyridinium, carbamoyl substituted pyridinium (particularly where the carbamoyl group is in the 4-position), or heterothio; $R_4$ is cyclohexenyl, cyclohexadienyl, phenyl, benzyl, phenethyl, substituted phenyl, benzyl, or phenethyl wherein the substituent is on the phenyl ring and is one or two members selected from chloro, bromo, methyl, ethyl, methoxy, ethoxy and hydroxy, or a substituted or unsubstituted heterocyclic selected from 2-thienyl, 3-thienyl, 2-furyl, 3-furyl, 2-pyridyl, 3-pyridyl and 4-pyridyl wherein heterocyclic substituent is chloro, bromo, methyl, or ethyl; $R_2$ is straight or branched chain alkenyl or alkinyl of 2 to 4 carbons; and $R_3$ is hydrogen or straight or branched chain alkyl or 1 to 4 carbons.

Also preferred as both final products and intermediates are the compounds of formula I wherein X is

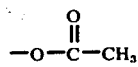

and $R_2$, $R_3$, and $R_4$ are as defined above.

The most preferred final compounds are the acids and alkali metal salts of formula I wherein $R_4$ is 2-thienyl, 3-thienyl, phenyl, or 4-hydroxyphenyl; X is heterothio, particularly wherein X is

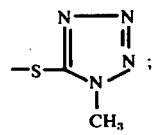

and $R_2$ is straight or branched chain alkenyl of 2 to 4 carbons.

The acid compounds of formula I have a broad spectrum of antibacterial activity against both gram positive and gram negative organisms such as *Staphylococcus aureus*, *Salmonella schottmuelleri*, *Proteus rettgeri*, *Escherichia coli*, *Enterobacter cloacae*, *Klebsiella pneumoniae*, etc. They may be used as antibacterial agents in a prophylactic manner, e.g., in cleaning or as surface disinfecting compositions, or otherwise to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg., daily, orally or parenterally, in single or two to four divided doses to treat infections of bacterial origin, e.g. 5.0 mg./kg. in mice.

Up to about 600 mg. of an acid compound of formula I or a physiologically acceptable salt thereof may be incorporated in an oral dosage form such as tablets, capsules or elixirs or in an injectable form in a sterile aqueous vehicle prepared according to conventional pharmaceutical practice.

They may also be used in cleaning or disinfecting compositions, e.g., for cleaning barns or dairy equipment, at a concentration of about 0.2 to 1% by weight or such compounds admixed with, suspended or dissolved in conventional inert dry or aqueous carriers for application by washing or spraying.

They are also useful as nutritional supplements in animal feeds.

Illustrative process details are provided in the examples for the various reactions. All temperatures are on the centigrade scale.

EXAMPLE 1

7β-[[D-[[(2-Propenylamino)carbonyl]amino]-2-thienylacetyl]amino]-3-[[(1-methyl-1H-tetrazol-5-yl)thio]methyl]-8-oxo-5-thia-1-azobicyclo[4.2.0]oct-2-ene-2-carboxylic acid a. D-α-[[(2-Propenylamino)carbonyl]amino]-2-thiopheneacetic acid, 4-nitrophenyl ester To a solution of 0.01 mole of D-α-isocyanato-2-thiopheneacetic acid, 4-nitrophenyl ester in 20 ml. of tetrahydrofuran is added dropwise at room temperature over 30 minutes a solution of 0.63 g. of 2-propen-1-amine in 10 ml. of tetrahydrofuran. The mixture is stirred for 1 hour. After concentrating the solution and treating the residue with ether, 3.4 g. of D-α-[[(2-propenylamino)cabonyl]amino]-2-thiopheneacetic acid, 4-nitrophenyl ester are obtained as an amorphous powder; m.p. 98°–102°.

b. 7β-Amino-3-[[(1-methyl-1H-tetrazol-5-yl)thio]methyl]-8-oxo-5-thia-1-azabicyclo[4.2.0]oct-2-ene-2-carboxylic acid To a stirred suspension of 27.2 g. 7-amino cephalosporanic acid (0.1 mole) in 150 ml. of acetone and 100 ml. of $H_2O$ at 0°14 5° is added 50 ml. of 2N NaOH, with care being taken to keep the pH below 8.5. A solution of 12.7 g. (0.11 mole) of 1-methyl-5-mercapto-1H-tetrazole in 50 ml. of 2N NaOH is added, and the mixture is allowed to warm to room temperature. The stirred mixture is then maintained at 60° (internal temperature) under nitrogen for 3 hours at pH 7–7.5 by the periodic addition of dilute aqueous NaOH. The mixture is cooled in an ice-water bath, and while stirring, 3N HCl is added to adjust the pH to 3.9. Stirring is continued for 15 minutes, and the precipitate is collected by filtration, washed with water, and then acetone, and finally dried to give the desired product as a powder (18.4 g.).

c. 7β-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester A mixture of 16.4 g. (0.05 mole) of the acid product from part (b), 10.3 g. (0.054 mole) p-toluenesulfonic acid monohydrate, 350 ml. of dioxane (dried by passage through basic alumina), and dry $CH_3OH$ is stirred at room temperature under nitrogen for 30 minutes. The clear solution is evaporated to a residue, and $H_2O$ and $CH_3OH$ are removed by four evaporations of 100 ml. quantities of dioxane. Fresh dioxane (300 ml.) is then added to the residue followed by a solution of crystalline diphenyldiazomethane (19.4 g., 0.10 mole) in 150 ml. of dry dimethoxyethane. The mixture is initially shaken vigorously for 10–15 minutes and then stirred at room temperature for 3 hours. Methanol (25 ml.) is added, and the red solution is stirred until it has turned yellow-orange. The solvents are removed in vacuo, and the residue is treated with 400 ml. of $CH_2Cl_2$ and a solution of 20 g. of $K_2HPO_4$ in 250 ml. of $H_2O$. The $CH_2Cl_2$ layer is washed with water and saturated NaCl, and finally dried ($MgSO_4$) to give a residue after removal of the solvent in vacuo. Treatment of the residue with $Et_2O$ gives a solid (27 g.). Column chromatorgraphy of this solid on silica gel by elution with $CHCl_3$ and then EtOAc—$CHCl_3$ (4:1) provides the desired product as a residue (12.9 g.). Treatment with EtOAc then provides 8.0 g. of the desired product as a pale yellow powder.

d. 7β-[[D-[[(2-Propenylamino)carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-caboxylic acid, diphenylmethyl ester 1.48 g. (0.003 mole) of 7β-amino-3-[[(1-methyl-1H-tetrazol-5-yl)thio]methyl]-8-oxo-5-thia-1-azabicyclo[4.2.0]-oct-2-ene-2-carboxylic acid, diphenylmethyl ester from part (c) are dissolved in 20 ml. of methylene chloride and a solution of 1.15 g. (0.0035 mole) of D-α-[[(2-propenylamino)carabonyl]-amino]-2-thiopheneacetic acid, 4-nitrophenyl ester from part (a) in 10 ml. of N,N-dimethylacetamide is added. After the addition of 0.49 g. (0.003 mol.) of hydroxybenzotriazole, the solution is stirred overnight at room temperature. The reaction solution is diluted with 250 ml. of ethylacetate, washed with sodium bicarbonate solution and with water, dried with magnesium sulfate and concentrated in vacuum. The residue is triturated with ether and filtered under suction to obtain 1.5 g. of 7β-[[D-[[(2-propenylamino)carbonyl]amino]-2-thienyl-acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester as a yellow-brown amorphous powder; m.p. 116°.

e. 7β-[[D-[[(2-Propenylamino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid 1.6 g. of the diphenylmethyl ester product from part (d) is reacted with 10 ml. of anisole and 17 ml. of trifluoroacetic acid at 0°–5° for 10 minutes to obtain 1.2 g. of 7β-[[D-[[(2-propenylamino)carbonyl]amino]-2-thienylacetyl]amino]-3-[[(1-methyl-1H-tetrazol-5-yl)thio]methyl]-8-oxo-5-thia-1-azabicyclo-[4.2.0]oct-2 -ene-2-carboxylic acid as a yellow-brown powder; m.p. 120° (dec.).

An aqueous equimolar solution of this acid and sodium bicarbonate is lyophilized to yield 7β-[[D-[[2-propenylamino)-carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt; m.p. 160°–163° (dec.).

In an analogous manner, by substituting L-α-isocyanato- 2-thienylacetic acid, 4-nitrophenyl ester for the D-isomer in part (a) and then following the procedure of example 1, one obtains 7β-[[L-[[(2-propenylamino)carbonyl]amino]-2-thienylacetyl]amino]-3-[[(1-methyl-1H-tetrazol-5-yl)thio[methyl[-8-oxo-5-thia-1-azabicyclo[4.2.0]oct-2-ene-2-carboxylic acid and its sodium salt.

EXAMPLE 2

7α-Methoxy-7β-[[D-[[(2-propenylamino)carabonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid a. 7α-Methoxy-7β-[[D-[[(2-propenlyamino)carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid, diphenylmethyl ester D-α-[[(2-Propenylamino)cabonyl]amino]-2-thiopheneacetic acid, 4-nitrophenyl ester from example 1(a) and 7α- methoxy-7β-amino-3-[[(1-methyl-1H-tetrazol-5-yl)thio]methyl]-8-oxo-5-thia-1-azabicyclo4.2.-0]oct-2-ene-2-carboxylic acid, diphenylmethyl ester are reacted according to the procedure of example 1 (d) to yield 7α-methoxy-7β-[[D-[[(2-propenylamino)-carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-caraboxylic acid, diphenylmethyl ester.

b. 7α-Methoxy-7β-[[D-[[(2-propenylamino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid The diphenylmethyl ester product from part (a) is treated with anisole and trifluoroacetic acid according to the procedure of example 1 (e) to yield 7α-methoxy-7β-[[D-[[(2-propenylamino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid.

An aqueous equimolar solution of this acid and sodium bicarbonate is lyophilized to yield 7α-methoxy-7β-[[D-[[(2-propenylamino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt.

In an analogous manner one can obtain, 7α-methoxy-7β- [[L-[[(2-propenylamino)carabonyl]amino]-2-thienylacetyl]amino ]-3-[[(1-methyl-1H-tetrazol-5-yl)thio]methyl]-8-oxo-5-thia-1-azabicyclo[4.2.0]oct-2-ene-2-caboxylic acid and its sodium salt.

EXAMPLES 3–50

Following the procedure of example 1 but employing the isocyanato compound of Col. I and the amine of Col. II one obtains the nitrophenyl ester of Col. III. The ester of Col. III and the 7β-amino-7α-methoxy or desmethoxy-cephalosporanic acid ester of Col. IV are reacted to yield the acylated cephalosporanic acid ester of Col. V. The ester of Col. V can be treated to remove the ester protecting group and yield the cephalosporanic acid of Col. VI which can be converted by known means to yield the corresponding salt.

Col. I

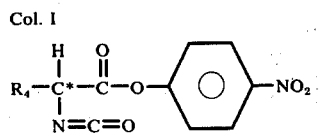

Col. II

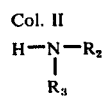

Col. III

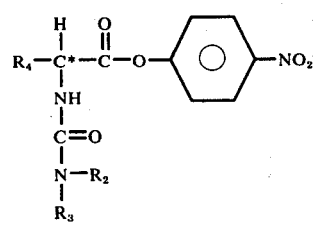

Col. IV

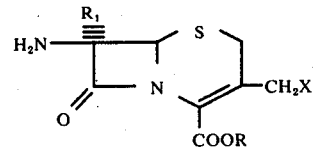

-continued

Col. V 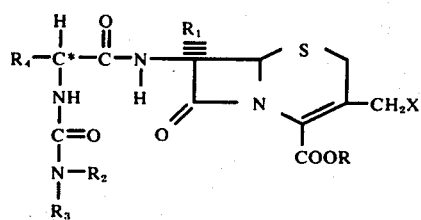

Col. VI 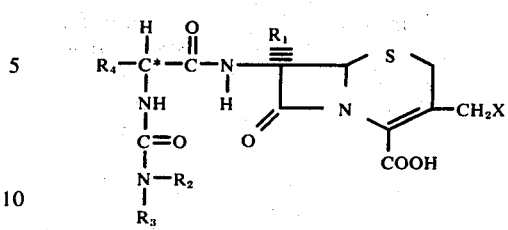

| Ex. | R₄ | R₂ | R₃ | R₁ | R | X |
|---|---|---|---|---|---|---|
| 3 | 2-thienyl | −CH₂−CH=CH₂ | −CH₃ | −H | −CH(C₆H₅)₂ | −S-tetrazolyl-N-CH₃ |
| 4 | 2-thienyl | −CH₂−CH=CH₂ | −CH₃ | −OCH₃ | −CH(C₆H₅)₂ | −S-tetrazolyl-N-CH₃ |
| 5 | 2-thienyl | −CH=CH₂ | −H | −H | −CH₂−C₆H₅ | −S-thiadiazolyl-CH₃ |
| 6 | 2-thienyl | −CH=CH₂ | −H | −OCH₃ | t-C₄H₉ | −S-tetrazolyl-N-C₂H₅ |
| 7 | 5-chloro-2-thienyl | −CH(CH₃)−CH=CH₂ | −H | −H | −CH₂CCl₃ | −S-oxadiazolyl-CH₃ |
| 8 | 5-methyl-2-thienyl | −CH₂−CH=CH−CH₃ | −H | −OCH₃ | −C₂H₅ | −O−C(O)−CH₃ |
| 9 | 2-thienyl | −CH₂−CH=CH−CH₃ | −C₂H₅ | −H | −CH(C₆H₅)₂ | −O−C(O)−CH₃ |
| 10 | 2-thienyl | −CH(C₂H₅)−CH=CH₂ | −H | −H | −CH₂−C₆H₅ | −S-thiazolyl-CH₃ |
| 11 | 2-thienyl | −C(CH₃)₂−CH=CH₂ | −H | −H | −CH(C₆H₅)₂ | −S-tetrazolyl-N-CH₃ |
| 12 | 2-thienyl | −CH−CH=CH₂ | −OCH₃ | −OCH₃ | −CH₂CCl₃ | −S-thiadiazolyl |
| 13 | 2-thienyl | −CH₂−C≡CH | −H | −H | −CH(C₆H₅)₂ | −O−C(O)−C₂H₅ |
| 14 | 2-thienyl | −CH₂−C≡CH | −C₂H₅ | −OCH₃ | t-C₄H₉ | −S-tetrazolyl-N-CH₃ |
| 15 | 2-thienyl | −CH₂−C≡C−CH₃ | −H | −H | −CH(C₆H₅)₂ | −S-thiazolyl-CH₃ |

-continued

| Ex. | R₄ | R₂ | R₃ | R₁ | R | X |
|---|---|---|---|---|---|---|
| 16 |  | −CH−C≡CH<br>    │<br>    C₂H₅ | −CH₃ | −OCH₃ | −CH₂−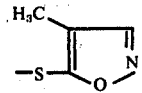 |  |
| 17 | 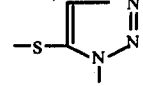 |     CH₃<br>    │<br>−C−C≡C−C₂H₅<br>    │<br>    CH₃ | −H | −H | −CH()₂ | 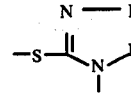 |
| 18 | 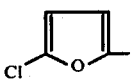 | −CH₂−CH=CH₂ |        CH₃<br>       │<br>−CH₂−CH<br>       │<br>       CH₃ | −H | −CH(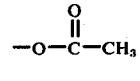)₂ |  |
| 19 | 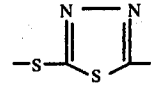 | −CH=CH₂ | −H | −OCH₃ | t-C₄H₉ | O<br>‖<br>−O−C−CH₃ |
| 20 |  | −CH−CH=CH₂<br>    │<br>    CH₃ | −CH₃ | −H | −CH₂−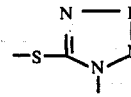 |  |
| 21 | 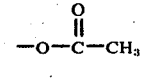 | −CH₂−C≡CH | −H | −H | −CH(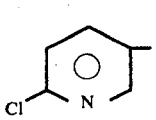)₂ | 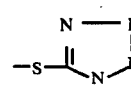 |
| 22 |  | −CH−CH=CH−CH₃<br>    │<br>    CH₃ | −C₂H₅ | −OCH₃ | −CH(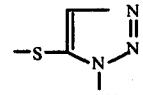)₂ | O<br>‖<br>−O−C−CH₃ |
| 23 |  | −CH₂−C≡CH | −H | −OCH₃ | −CH₂CCl₃ | 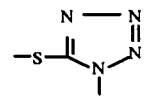 |
| 24 |  | −CH=CH₂ | −C₂H₅ | −H | −CH(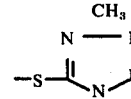)₂ |  |
| 25 | 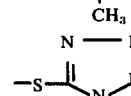 | −CH₂−CH=CH₂ | −H | −H | −CH(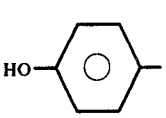)₂ | 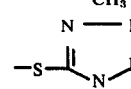 |
| 26 | 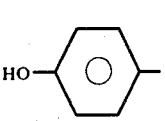 | −CH₂−CH=CH₂ | −CH₃ | −OCH₃ | −CH(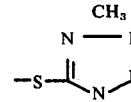)₂ |  |
| 27 | 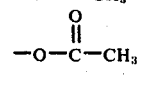 | −CH=CH₂ | −H | −OCH₃ | −CH₂− |  |
| 28 |  | −CH=CH₂ | −H | −H | t-C₄H₉ |  |
| 29 |  | −CH=CH₂ | −C₂H₅ | −OCH₃ | −CH₂CCl₃ |  |
| 30 |  | −CH−CH=CH−CH₃<br>    │<br>    CH₃ | −H | −H | −CH()₂ | O<br>‖<br>−O−C−CH₃ |

-continued

| Ex. | R₄ | R₂ | R₃ | R₁ | R | X |
|---|---|---|---|---|---|---|
| 31 | 3,5-dichlorophenyl | $-\underset{\underset{CH_3}{\mid}}{\overset{\overset{CH_3}{\mid}}{C}}-CH=CH_2$ | —H | —OCH₃ | —CH₂—phenyl | $-S-\underset{S}{\overset{N-N}{\underset{\parallel}{\diagdown\!\!\diagup}}}-CH_3$ (1,3,4-thiadiazole) |
| 32 | 4-methylphenyl | $-\underset{\underset{C_2H_5}{\mid}}{CH}-CH=CH_2$ | —C₃H₇ | —H | —CH(phenyl)₂ | $-S-\underset{O}{\overset{N-N}{\underset{\parallel}{\diagdown\!\!\diagup}}}-CH_3$ (1,3,4-oxadiazole) |
| 33 | phenyl | —CH₂—C≡CH | —H | —OCH₃ | —CH(phenyl)₂ | $-S-\underset{\underset{CH_3}{\mid}}{\overset{N-N}{\underset{N\diagdown\!\!\!N}{\diagdown\!\!\diagup}}}$ (1-methyltetrazole) |
| 34 | 4-hydroxyphenyl | —CH₂—C≡CH | —CH₃ | —H | —CH(phenyl)₂ | (1-methyltetrazol-5-ylthio) |
| 35 | benzyl | —CH=CH₂ | —H | —OCH₃ | —CH(phenyl)₂ | (1-methyltetrazol-5-ylthio) |
| 36 | 4-hydroxybenzyl | $-\underset{\underset{CH_3}{\mid}}{CH}-CH=CH_2$ | —H | —H | t-C₄H₉ | $-O-\overset{\overset{O}{\parallel}}{C}-CH_3$ |
| 37 | benzyl | —CH₂—C≡C—CH₃ | —H | —OCH₃ | —CH(phenyl)₂ | (1-methyltetrazol-5-ylthio) |
| 38 | —H | —CH₂—CH=CH—CH₃ | —C₂H₅ | —H | —CH(phenyl)₂ | (1-methyltetrazol-5-ylthio) |
| 39 | —C₂H₅ | —CH₂—C≡CH | —H | —OCH₃ | —CH(phenyl)₂ | $-S-\underset{O}{\overset{N-N}{\underset{\parallel}{\diagdown\!\!\diagup}}}-CH_3$ |
| 40 | cyclohexyl | —CH=CH₂ | $-CH_2-\underset{\underset{CH_3}{\mid}}{\overset{\overset{CH_3}{\mid}}{CH}}$ | —H | —CH(phenyl)₂ | $-S-\underset{\underset{H}{\mid}}{\overset{N=N}{\underset{N}{\diagdown\!\!\diagup}}}$ |
| 41 | cyclohexyl | $-\underset{\underset{CH_3}{\mid}}{CH}-C≡CH$ | —H | —OCH₃ | —CH(phenyl)₂ | (1-methyltetrazol-5-ylthio) |
| 42 | cyclohexenyl | —CH₂—CH=CH₂ | —CH₃ | —H | —CH(phenyl)₂ | (1-methyltetrazol-5-ylthio) |
| 43 | cyclohexenyl | —CH₂—C≡CH | —H | —OCH₃ | —CH(phenyl)₂ | (1-methyltetrazol-5-ylthio) |
| 44 | cyclohexadienyl | $-\underset{\underset{C_2H_5}{\mid}}{CH}-CH=CH_2$ | —H | —H | —CH(phenyl)₂ | (1-methyltetrazol-5-ylthio) |

-continued

| Ex. | R₄ | R₂ | R₃ | R₁ | R | X |
|---|---|---|---|---|---|---|
| 45 | phenyl | $-CH_2-C \equiv CH$ | $-CH_3$ | $-H$ | $-CH(C_6H_5)_2$ | 1-methyl-1H-tetrazol-5-ylthio |
| 46 | 2-thienyl | $-CH_2-CH=CH_2$ | $-H$ | $-H$ | $-CH_2-O-C(=O)-CH_3$ | 1-methyl-1H-tetrazol-5-ylthio |
| 47 | phenyl | $-CH_2-C \equiv C-CH_3$ | $-H$ | $-OCH_3$ | $-CH(CH_3)-O-C(=O)-C_2H_5$ | 5-methyl-1,3,4-thiadiazol-2-ylthio |
| 48 | 4-hydroxyphenyl | $-CH(CH_3)-CH=CH_2$ | $-H$ | $-H$ | $Si(CH_3)_3$ | 1-methyl-1H-tetrazol-5-ylthio |
| 49 | phenyl | $-CH_2-C \equiv C-C_2H_5$ | $-CH_3$ | $-OCH_3$ | $Si(CH_3)_3$ | 1-methyl-1H-tetrazol-5-ylthio |
| 50 | 2-thienyl | $-CH_2-C \equiv C-CH_3$ | $-C_2H_5$ | $-H$ | $-CH_2-O-C(=O)-C_3H_7$ | 1-ethyl-1H-tetrazol-5-ylthio |

The isocyanato compounds of Col. I may be in either the D- or L- form or may be a mixture of the D- and L- isomers.

The isocyanato compounds of Col. I may be in either the D- or L- form or may be a mixture of the D- L- isomers.

EXAMPLE 51

7 β-[[D-[[[(Ethenylamino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid a. D-2-[[[(4-Methoxyphenyl)methoxy]carbonyl]amino]-2-thiopheneacetic acid 74 g. of D-2-Thienylglycine are dissolved in 940 ml. of water. 37.8 g. of magnesium oxide are added and to this resulting suspension a solution of 107.5 g. of p-methoxybenzyloxycarbonylazide in 940 ml. of dioxane is added with stirring. The mixture is stirred at room temperature for 24 hours. It is then filtered and the filtrate is extracted with 600 ml. of ether. The extract is discarded. The water is dioxane phase is layered over with 600 ml. of ethyl acetate, cooled to 5° and brought to pH 2 with 2N hydrochloric acid. The layers are separated and the aqueous layer is again extracted with 300 ml. of ethyl acetate. The combined ethyl acetate extracts are washed with water, dried with magnesium sulfate, filtered and concentrated. The oily residue crystallizes upon trituration with petroleum ether to yield 118 g. of D-2-[[[(4-methoxyphenyl)methoxy]carbonyl]amino]-2-thiopheneacetic acid; m.p. 84°–94°; [α]₂₀ ᴰ: −69° (c=1, tetrahydrofuran).

b. 7β-[[D-[[[(4-Methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 46.2 g. of 7β-amino-3-[[(1-methyl-1H-tetrazol-5-yl)thio]methyl]-8-oxo-5-thia-1-azabicyclo[4.2.0.]oct-2-ene-2carboxylic acid, diphenylmethyl ester from example 1(c) are dissolved in 550 ml. of anhydrous methylene chloride. 550 ml. of tetrahydrofuran and 36 g. of D-2-[[[(4-methoxyphenyl)methoxy]carbonyl]amino]-2-thiopheneacetic acid, from part (a), are added. The reaction solution is cooled to 0° and a solution of 22.5 g. of dicyclohexylcarbodiimide in 150 ml. of anhydrous tetrahydrofuran is added dropwise over the course of 30 minutes. The mixture is then stirred for 90 minutes at 0° and finally 120 minutes at room temperature. The precipitated dicyclohexylurea (21 g.) is filtered off under suction and the filtrate is concentrated. The residue is taken up in a mixture of 1000 ml. of ethyl acetate and 400 ml. of tetrahydrofuran, filtered and the filtrate is washed first with sodium bicarbonate solution and then with water. This is then dried with magnesium sulfate, treated with activated carbon, filtered and the filtrate is then concentrated slowly under vacuum to a small volume. After standing overnight in the refrigerator, the precipitate crystals are filtered under suction to obtain 63.1 g. of 7β-[[D-[[[(4-methoxyphenyl)methoxy]carbonyl]amino]-2-thienylacetyl]amino]-3-[[81-methyl-1H-tetrazol-5-yl)thio]methyl]-8-oxo-5-thia-1-azabicyclo[4.2.0]oct-2-ene-2-carboxylic acid, diphenylmethyl ester; m.p. 130°–131° (dec.). [α]₂₀ ᴰ: -117° (c=1, tetrahydrofuran).

c. 7β-[D-2-Amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1)

62 g. of the diphenylmethyl ester product from part (b) are added to 300 ml. of anisole with stirring. The mixture is cooled to 0° and 750 ml. of trifluoroacetic acid are added slowly. The mixture is stirred for 10 minutes at 0° and the anisole is evaporated at 0.1 mm. of Hg. and 35° bath temperature. The residue is treated with 250 ml. of petroleum ether, then 350 ml. of ether, stirred for one hour, and filtered with suction to yield 46.4 g. of 7β-[D-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1); m.p. 138°-139° (dec.).

d. 7β-[[D-[[(Ethenylamino)carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid 0.01 mole of the trifluoroacetic salt product from part (c) are suspended in methylene chloride and 0.02 mole of triethylamine are added. To the almost clear solution is added dropwise at 0°-5°,0.012 mole of a solution of isocyanatoethene and methylene chloride. After stirring for 1 hour, the reaction solution is concentrated, the residue is dissolved in water, filtered, and acidified with 2N hydrochloric acid to yield as a precipitate, 7β-[[D-[[(ethenylamino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid.

An aqueous equimolar solution of this acid and sodium bicarbonate is lyophilized to yield 7β-[[D-[[(ethenylamino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt.

In an analogous manner by substituting L-2-thienylglycine for the D-isomer in part (a) and then following the procedure of example 51, one obtains 7β-[[L-[[(ethenylamino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid and its sodium salt.

EXAMPLE 52

7α-Methoxy-7β-[[D,L-[[(ethenylamino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid a. 7α-Methoxy-7β-[[D,L-[[[(4-methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 2.41 g. (0.0075 mole) of D,L-2-[[[(4-methoxyphenyl)methoxy]carbonyl]amino]-2-thiopheneacetic acid (prepared according to the procedure of example 51 (a)) is dissolved in 50 ml. of dry methylene chloride, the solution is cooled in an ice bath to 0°-5°, and 0.969 g. (0.0075 mole) of diisopropylethylamine and isobutylchloroformate are added to the cold solution. After 10 minutes, 3.28 g. (0.00625 mole) of 7β-amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester is added to the reaction mixture and the ice bath is removed. Following 3 hours of stirring at room temperature, a second portion of mixed anhydride is prepared in a separate flask using the procedure described above. This solution is added to the reaction mixture and after 4.5 hours another batch of mixed anhydride prepared using half the quantities set forth above is added to the main reaction mixture. Stirring is continued at room temperature for 12 hours and the reaction mixture is then diluted with methylene chloride and washed with water, saturated aqueous sodium bicarbonate solution, and water. The organic layer is dried over sodium sulfate and the solvent is removed in vacuo to yield a foam. This crude product is chromatographed on silica gel (200 g., 60-200 mesh) and the desired product is eluted with 9:1 and 4:1 methylene chloride:ethyl acetate. The oily product is precipitated as a powder from a methylene chloride-ether mixture and dried over phosphorous pentoxide in vacuo to yield 3.81 g. of 7α-methoxy-7β-[[D,L-[[[(4-methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester. Alternatively, the titled compound can be obtained by the following procedure.

129 mg. (0.4 mmole) of D,L-2-[[[(4-methoxyphenyl)-methoxy]carbonyl]amino]-2-thiopheneacetic acid is dissolved in 2 ml. of anhydrous methylene chloride and 47 mg. (0.2 mmole) of dicyclohexylcarbodiimide is added. The mixture is stirred for 15 minutes at room temperature during which time colorless dicyclohexylurea crystallizes. The suspension is directly filtered into a stirring solution of 77 mg. (0.147 mmole) of 7β-amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester in 1 ml. of methylene chloride. After stirring at room temperature for 19 hours, the mixture is diluted with methylene chloride, washed with pH 7.4 buffer, and dried over sodium sulfate. Removal of solvent under reduced pressure yields a crude oil which is chromatographed on preparative thin layer chromatography silica gel plates developed in a 4:1 chloroform:ethyl acetate mixture. The desired product (58 mg.) is isolated as an oil.

b. 7α-Methoxy-7β-[D,L-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1)

The diphenylmethyl ester product from part (a) is reacted with trifluoroacetic acid in the presence of anisole according to the procedure of example 51(c) to yield the titled compound.

c. 7α-Methoxy-7β-[[D,L-[[(ethenylamino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid The trifluoroacetic acid salt product from part (b) is reacted with isocyanatoethene according to the procedure of example 51(d) to yield 7α-methoxy-7β-[[D,L-[[(ethenylamino)carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid.

An aqueous equimolar solution of this acid and sodium bicarbonate is lyophilized to yield 7α-methoxy-7β-[[D,L-[[(ethenylamino)carbonyl]amino]-2-thienylacetyl]amino]-3-[[(1-methyl-1H-tetrazol-5-yl)thio]methyl]-8-oxo-5-thia-1 -azabicyclo[4.2.0]oct-2-ene-2-carboxylic acid, sodium salt.

EXAMPLES 53-77

Following the procedure of example 51 but employing the acylating agent shown in Col. I and the 7β-amino-7α-methoxy or desmethoxy-cephalosporanic acid ester shown in Col. II, one obtains the protected ester shown in Col. III. The protecting group and ester group are removed as the compound of Col. III is converted to its trifluoroacetic acid salt shown in Col IV. The trifluoroacetic acid salt is reacted with the isocyanato compound of Col. V to yield the cephalosporanic acid shown in Col. VI. The acid of Col. VI can be reacted so as to reintroduce the ester group and yield the compound of Col. VII or can be treated according to known procedures to yield the corresponding salt.

Col. I $R_4-C^*H-COOH$

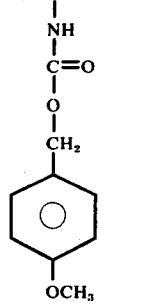

Col. II

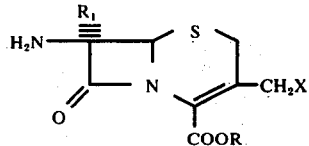

Col. III

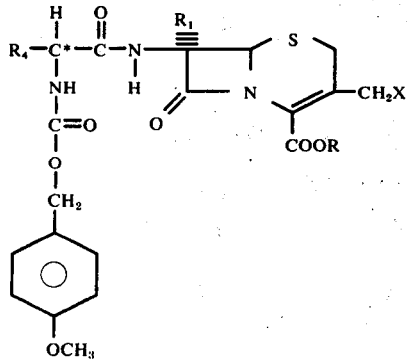

Col. IV

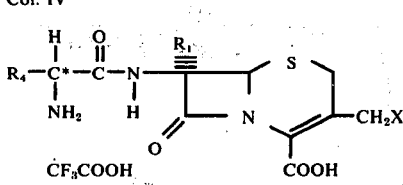

$CF_3COOH$

Col. V

$R_2-N=C=O$

Col. VI

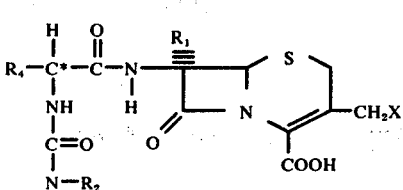

Col. VII

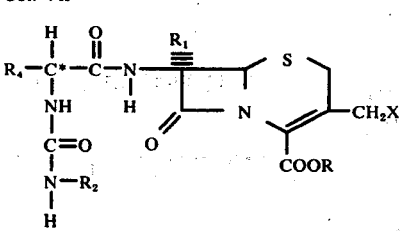

Alternatively, the α-aminocephalosporanic acid ester of Col. VIII can be treated with the compound of Col. V to yield the ester of Col. VII. This ester can then be treated to remove the ester group and yield the cephalosporanic acid of Col. VI.

Col. VIII

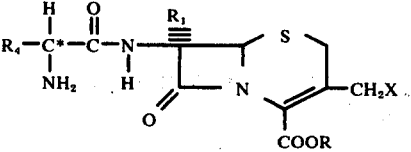

| Ex. | $R_4$ | $R_2$ | $R_1$ | R | X |
|---|---|---|---|---|---|
| 53 | 2-chlorothienyl | $-CH_2-CH=CH_2$ | $-H$ | $-CH_2-\text{phenyl}$ | $-S-\text{(1-methyl-tetrazolyl)}$ |
| 54 | thienyl | $-CH-CH=CH_2$ with $CH_3$ | $-OCH_3$ | $-CH(\text{phenyl})_2$ | $-S-\text{(1-methyl-tetrazolyl)}$ |
| 55 | thienyl | $-CH_2-C\equiv CH$ | $-H$ | $-CH(\text{phenyl})_2$ | $-S-\text{(1-methyl-tetrazolyl)}$ |

-continued

| Ex. | R₄ | R₂ | R₁ | R | X |
|---|---|---|---|---|---|
| 56 | thienyl (2-) | —CH₂—C≡C—CH₃ | —OCH₃ | —CH(C₆H₅)₂ | —S-(1-methyltetrazol-5-yl) |
| 57 | thienyl (2-) | —CH(C₂H₅)—C≡CH | —H | t-C₄H₉ | —S-(5-methyl-1,3,4-thiadiazol-2-yl) |
| 58 | furyl (2-) | —CH=CH₂ | —H | —CH(C₆H₅)₂ | —S-(1-methyltetrazol-5-yl) |
| 59 | furyl (2-) | —CH(CH₃)—CH=CH—CH₃ | —OCH₃ | —CH₂—C₆H₅ | —S-(5-methyl-1,3,4-oxadiazol-2-yl) |
| 60 | furyl (2-) | —CH(CH₃)—C≡C—CH₃ | —H | —CH(C₆H₅)₂ | —S-(1-methyltetrazol-5-yl) |
| 61 | furyl (2-) | —CH₂—CH=CH—CH₃ | —H | —CH(C₆H₅)₂ | —O—C(=O)—CH₃ |
| 62 | piperidyl | —CH₂—CH=CH₂ | —OCH₃ | —C₂H₅ | —S-(1,3,4-thiadiazol-2-yl) |
| 63 | pyridyl (4-) | —CH(CH₃)—C≡CH | —H | —CH(C₆H₅)₂ | —S-(1-ethyltetrazol-5-yl) |
| 64 | C₆H₅— | —CH₂—CH=CH₂ | —OCH₃ | —CH(C₆H₅)₂ | —S-(1-methyltetrazol-5-yl) |
| 65 | C₆H₅— | —CH₂—C≡C—CH₃ | —H | —CH(C₆H₅)₂ | —O—C(=O)—CH₃ |
| 66 | HO—C₆H₄— | —CH=CH₂ | —H | —CH(C₆H₅)₂ | —S-(4-methylisothiazol-5-yl) |
| 67 | H₃CO—C₆H₄— | —CH₂—C≡CH | —OCH₃ | —CH(C₆H₅)₂ | —S-(1H-tetrazol-5-yl) |
| 68 | C₆H₅—CH₂— | —C(CH₃)₂—CH=CH₂ | —H | —CH(C₆H₅)₂ | —S-(1-methyltetrazol-5-yl) |
| 69 | Cl—C₆H₄—CH₂— | —CH₂—C≡C—CH₃ | —OCH₃ | t-C₄H₉ | —S-(1-methyltetrazol-5-yl) |
| 70 | cyclohexyl | —CH₂—CH=CH₂ | —H | —CH(C₆H₅)₂ | —S-(1-methyltetrazol-5-yl) |

-continued

| Ex. | R₄ | R₂ | R₁ | R | X |
|---|---|---|---|---|---|
| 71 | cyclohexyl | —CH₂—C≡C—CH₃ | —OCH₃ | —CH(C₆H₅)₂ | -S-(1-methyl-tetrazol-5-yl) |
| 72 | cyclohexyl | —CH(CH₃)—CH=CH₂ | —H | —CH₂CCl₃ | -S-(1-methyl-tetrazol-5-yl) |
| 73 | cyclohexenyl | —CH₂—C≡C—CH₃ | —H | —CH(C₆H₅)₂ | -S-(1-methyl-tetrazol-5-yl) |
| 74 | phenyl | —CH(C₂H₅)—CH=CH₂ | —OCH₃ | —CH₂—O—C(=O)—CH₃ | -S-(1-methyl-tetrazol-5-yl) |
| 75 | 2-thienyl | —C(CH₃)—C≡CH | —H | —CH(CH₃)—O—C(=O)—CH₃ | -S-(5-methyl-1,3,4-thiadiazol-2-yl) |
| 76 | 4-hydroxyphenyl | —CH₂—CH=CH—CH₃ | —OCH₃ | Si(CH₃)₃ | -S-(5-methyl-1,3,4-oxadiazol-2-yl) |
| 77 | 2-thienyl | —CH₂—C≡C—CH₃ | —H | Si(CH₃)₃ | -S-(1-methyl-tetrazol-5-yl) |

EXAMPLE 78

7β-[[D-[[(Ethenylamino)carbonyl]amino]-2-thienylacetyl]amino]-3-[[4-(aminocarbonyl)-pyridino]methyl]-8-oxo-5-thia-1-azabicyclo[4.2.0]oct-2-ene-2-carboxylic acid a. 3-[(Acetyloxy)methyl-7β-[[D-[[[(4-methoxyphenyl)methoxy]carbonyl]amino]-2-thienylacetyl]amino]-8-oxo-5-thia-1-azabicyclo[4.2.0]oct-2-ene-2-carboxylic acid 3.2 g. (0.01 mole) of the D-2-[[[(4-methoxyphenyl)methoxy]carbonyl]amino]-2-thiopheneacetic acid from example 51(a) are brought into solution in 40 ml. of methylene chloride with 1.1 ml. of N-methylmorpholine. The solution is cooled to −15°, 1.39 ml. of isobutylchloroformate are added, and the mixture is stirred for 10 minutes. To this is added a solution of 3.26 g. (0.1012 mol) of 7-aminocephalosporanic acid and 3.1 ml. of triethylamine in 140 ml. of methylene chloride. The mixture is stirred for 1 hour at −5° and 1 hour at 5°. This mixture is then evaporated to dryness in a rotary evaporator. The solid residue is triturated with ether and filtered under suction. The substance is then dissolved in ice water, layered over with ethyl acetate and acidified to pH 2.5. The layers are separated, the aqueous layer is extracted once more with ethyl acetate, the combined ethyl acetate extracts are washed with water, dried with magnesium sulfate and concentrated. The residue (4.9 g.) is dissolved in 200 ml. of ethyl acetate and the solution is treated with activated carbon. After filtration, 2 g. of 3-[(acetyloxy)methyl]7β[[D-[[[(4-methoxyphenyl)methoxy]carbonyl]amino]-2-thienylacetyl]amino]-8-oxo-5-thia-1-azabicyclo[4.2.0]oct-2-ene-2-carboxylic acid, crystallize; m.p. 142°–143° (dec.).

b. 3-[(Acetyloxy)methyl]-7β-[D-2-amino-2-(2-thienyl)acetamido]-8-oxo-5-thia-1-azabicyclo[4.2.-0]oct-2-ene-2-carboxylic acid, trifluoroacetic acid salt (1:1)

2.0 g. of the product from part (a) are added at −5° to a mixture of 10 ml. of trifluoroacetic acid and 4 ml. of anisole. The mixture is stirred for 10 minutes and is then concentrated in a rotary evaporator. The residue is treated with ether and filtered to yield the titled compound.

c. 3-[(Acetyloxy)methyl]-7β-[[D-[[(ethenylamino)-carbonyl]amino]-2-thienylacetyl]amino]-8-oxo-5-thia-1-azabicyclo[4.2.0]oct-2-ene-2-carboxylic acid, sodium salt The trifluoroacetic acid salt product from part (b) is treated with isocyanatoethene according to the procedure of example 51(d) to yield 3-[(acetyloxy)methyl]-7β-[[D-[[(ethenylamino)carbonyl]amino]-2-thienylacetyl]amino]-8-oxo-5-thia-1-azabicyclo[4.2.-0]oct-2-ene-2-carboxylic acid.

An equimolar aqueous solution of this compound and sodium bicarbonate is lyophilized to yield 3-[(acetyloxy)methyl]-7β-[[D-[[(ethenylamino)carbonyl]amino]-2-thienylacetyl]amino]-8-oxo-5-thia-1-azabicyclo[4.2.0]oct-2-ene-2-carboxylic acid, sodium salt as a power.

d. 7β-[[D-[[(Ethenylamino)carbonyl]amino]-2-thienylacetyl]amino]-2-thienylacetyl]amino]- 3-[[4-(aminocarbonyl)pyridino]methyl]-8-oxo-5-thia-1-azabicyclo[4.2.0]oct-2-ene-2-carboxylic acid A mixture of 0.0005 mole of the sodium salt product of part (c), 0.0075 mole of 4-pyridinecarboxamide, 12 g. of potassium thiocyanate, and 7.5 ml. of water are heated at 50° for 24 hours. The clear solution is passed through a chromatography column filled with 150 g. of ion exchanger Amberlite XAD-2. The column is washed with about 3 liters of water and the tilted compound is eluted with a mixture of water:methanol (8:2). The methanol is evaporated from the eluate and the aqueous solution is lyophilized. The amorphous residue is triturated with ether and filtered under suction to yield 7β-[[D-[[(ethenylamino)carbonyl]amino]-2-thienylacetyl]amino]-3-[[4-(aminocarbonyl)pyridino]methyl]-8-oxo-5-thia-1-azabicyclo[4.2.0]oct-2-ene-2-carboxylic acid.

Similarly, by employing the L-2-[[[(4-methoxyphenyl)methoxy]carbonyl]amino]-2-thiopheneacetic acid in place of the D-isomer in the above procedure, one obtains 7β[[L-[[(ethenylamino)carbonyl]amino]-2-thienylacetyl]amino]-3-[[4-(aminocarbonyl)pyridino]methyl]-8-oxo-5-thia-1-azabicyclo[4.2.0]oct-2-ene-2-carboxylic acid.

EXAMPLES 79-93

Following the procedures of example 78, but employing the cephalosporanic acid sodium salt shown below in Col. I and the pyridine compound shown in Col. II, one obtains the product shown in Col. III.

Col. I

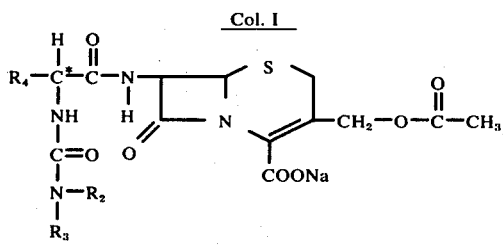

Col. II

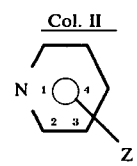

Col. III

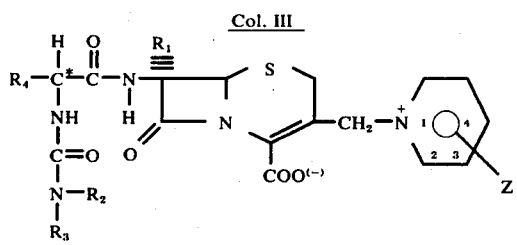

| Ex. | $R_1$ | $R_2$ | $R_3$ | $R_4$ | Z |
|---|---|---|---|---|---|
| 79 | —H | —CH=CH$_2$ | —H | phenyl | —C(O)—NH$_2$ (4) |
| 80 | —OCH$_3$ | —CH$_2$—C≡CH | —H | phenyl | —C(O)—NH$_2$ (4) |
| 81 | —OCH$_3$ | —CH$_2$—CH=CH$_2$ | —H | 2-thienyl | —H |
| 82 | —OCH$_3$ | —CH$_2$—C≡C—CH$_3$ | —H | phenyl | —H |
| 83 | —H | —CH$_2$—CH=CH—CH$_3$ | —CH$_3$ | 5-chloro-2-thienyl | —C(O)—NH$_2$ (3) |
| 84 | —OCH$_3$ | —CH(CH$_3$)—CH=CH$_2$ | —H | phenyl | —C(O)—NH$_2$ (3) |
| 85 | —H | —C(CH$_3$)—C≡C—CH$_3$ | —C$_2$H$_5$ | 4-hydroxyphenyl | —C(O)—NH$_2$ (2) |
| 86 | —OCH$_3$ | —CH(C$_2$H$_5$)—CH=CH$_2$ | i-C$_3$H$_7$ | phenyl | —H |
| 87 | —H | —CH(C$_3$H$_7$)—C≡CH | —H | 2-furyl | —C(O)—NH$_2$ (4) |
| 88 | —OCH$_3$ | —CH=CH$_2$ | —CH$_3$ | pyridyl | —H |

-continued

| Ex. | R₁ | R₂ | R₃ | R₄ | Z |
|---|---|---|---|---|---|
| 89 | —H | —CH₂—CH=CH₂ | —H |  | $\overset{O}{\underset{\|}{-C}}-NH_2 \,(4)$ |
| 90 | —OCH₃ | —CH₂—C≡CH | —CH₃ |  | —H |
| 91 | —H | $-\underset{\underset{CH_3}{\|}}{\overset{\overset{CH_3}{\|}}{C}}-CH=CH_2$ | —H | 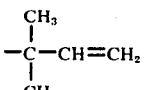 | —H |
| 92 | —OCH₃ | $-\underset{\underset{CH_3}{\|}}{\overset{\overset{CH_3}{\|}}{CH}}-C\equiv CH$ | —CH₃ |  | $\overset{O}{\underset{\|}{-C}}-NH_2 \,(4)$ |
| 93 | —H | $-\underset{\underset{C_2H_5}{\|}}{CH}-CH=CH_2$ | —H | 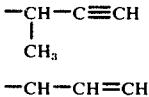 | $\overset{O}{\underset{\|}{-C}}-NH_2 \,(4)$ |

The cephalosporanic acid sodium salts shown above in Col. I may be in the D- or L-isomer form or a mixture of D- and L- isomers.

EXAMPLE 94

7β-[[D-[[ (Ethenylamino) carbonyl]amino]-2-thienylacetyl]amino]-3-[[(1-oxo-2-pyridinyl) thio]methyl]-8-oxo-5-thia-1-azabicyclo[4.2.0]oct-2-ene-2-carboxylic acid 0.003 mole of 3-[(acetyloxy)methyl]-7β-[[D-[[(ethenylamino) carbonyl]amino]-2-thienylacetyl] amino]-8-oxo-5-thia-1- azabicyclo [4.2.0] oct-2-ene-2-carboxylic acid, sodium salt from example 78 (c) and 0.004 mole of 2-mercaptopyridine, 1-oxide, sodium salt are dissolved in 15 ml. of water and heated overnight at 50°. The reaction mixture is then diluted with water, filtered, and the clear solution is adjusted to a pH of 2 by the addition of 2N hydrochloric acid. The resulting precipitate is filtered under suction to obtain 7β-[[D-[[(ethenylamino) carbonyl]amino]-2-thienylacetyl]amino]-3-[[(1-oxo-2-pyridinyl)thio]methyl]-8-oxo-5-thia-1-azabicyclo[4.2.0]oct-2-ene-2-carboxylic acid.

Following the same procedure but employing 3-[(acetyloxy)-methyl]-7β-[[L-[[(ethenylamino) carbonyl]amino]-2-thienylacetyl]-amino]-8-oxo-5-thia-1-azabicyclo [4.2.0]oct-2-ene-2-carboxylic acid, sodium salt, one obtains the corresponding final product in the L- form.

Similarly, the various 3-[(acetyloxy) methyl-7α-methoxy or desmethoxy-7β-acylureido-cephalosporanic acid sodium salts shown in Col. I of examples 79 to 93 may be employed in the procedure of example 94 to obtain other 3-[[(1-oxo-2-pyridinyl) thio]methyl]-cephalosporins within the scope of the invention.

EXAMPLE 95 7β-[[D-[[(Ethenylamino) carbonyl]amino]-2thienylacetyl]amino]-3-[[(1-oxopyridazin-3-yl) thio]methyl]-8-oxo-5-thia-1-azabicyclo[4.2.0]oct-2-ene-2-carboxylic acid 3-[(Acetyloxy) methyl]-7β-[[D-[[(ethenylamino) carbonyl]-amino]-2-thienylacetyl]amino]-8-oxo-5-thia-1-azabicyclo [4.2.0]- oct-2-ene-2-carboxylic acid, sodium salt from example 78 (c) is dissolved in a mixture of acetone:water (1:1). 1-Oxopyridazine-3-thiol, sodium salt is added under nitrogen and the solution is heated for several hours at 60°. The solution is diluted with 150 ml. of water and acidified to pH 5 by the addition of 2N hydrochloric acid while cooling. A precipitate forms which is filtered under suction to yeild 7β-[[D-[[(ethenylamino) carbonyl]amino]-2-thienylacetyl]amino]-3-[[(1-oxopyridazin-3-yl) thio]-methyl]-8-oxo-5-thia-1-azabicyclo[4.2.0]oct-2-ene-2-carboxylic acid.

Following the same procedure but employing 3-[(acetyloxy) methyl]-7β-[[L-[[(ethenylamino) carbonyl]amino]-2-thienylacetyl]amino]-8-oxo-5-thia-1-azabicyclo [4.2.9]oct-2-ene-2-carboxylic acid, sodium salt, one obtains the corresponding final product in the L-form.

EXAMPLES 96–104

Following the procedure of example 95 but substituting for the 1-oxopyridazine-3-thiol one of the following:

2-oxopyridazine-3-thiol 6-methyl-1-oxopyridazine-3-thiol 6-methoxy-1-oxopyridazine-3-thiol 6-t-butyl-2-oxopyridazine-3-thiol 6-ethyl-2-oxopyridazine-3-thiol 6-hydroxy-1-oxopyridazine-3-thiol 6-hydroxy-2-oxopyridazine-3-thiol 6-chloro-1-oxopyridazine-3-thiol 6-chloro-2-oxopyridazine-3-thiol one obtains:

7β-[[D-[[(ethenylamino) carbonyl]amino]-2-thienylacetyl]amino]-3-[[(2-oxopyridazin-3-yl) thio]methyl]-8-oxo-5thia-1-azabicyclo [4.2.0]oct-2-ene-2-carboxylic acid, 7β-[[D-[[(ethenylamino) carbonyl]amino]-2-thienylacetyl]amino]-3[[(6-methyl-1-oxopyridazin-3-yl) thio]methyl]-8-oxo-5-thia-1azabicyclo [4.2.0]oct-2-ene-2-carboxylic acid, 7β-[[D-[[(ethenylamino) carbonyl]amino]-2-thienylacetyl]amino]-3-[[(6-methoxy-1-oxopyridazin-3-yl) thio]methyl]-8-oxo-5-thia-1-azabicyclo [4.2.0]oct-2-ene-2-carboxylic acid, 7β-[[D-[[(ethenylamino) carbonyl]amino]-2-thienylacetyl]amino]-3-[[(6-t-butyl-2-oxopyridazin-3yl) thio]methyl]-8-oxo-5-thia-1-azabicyclo [4.2.0]oct-2-ene-2-carboxylic acid, 7β-[[D-[[(ethenylamino) carbonyl]amino]-2-thienylacetyl]amino]-3-[[(6-ethyl-2-ocopyridazin-3-yl) thio]methyl]-8-oxo-5-thia-1-azabicyclo [4.2.0]oct-2-ene-2-carboxylic acid, 7β-[[D-[[(ethenylamino) carbonyl]amino]-2-thienylacetyl]amino]-3-[[(6-hydroxyl-1-oxopyridazin-3-yl)thio]methyl]-8-oxo-5-thia-1-azabicyclo [4.2.0]oct-2-ene-2-carboxylic acid, 7β-[[D-[[(ethenylamino) carbonyl]amino]-2-thienylacetyl]amino]-3-[[(6-hydroxy-2-oxopyridazin-3-yl) thio]methyl]-8-oxo-5-thia-1-azabicyclo [4.2.0]oct-2-ene-2-carboxylic acid, 7β-[[D-[[(ethenylamino) carbonyl]amino]-2-thienylacetyl]amino]-3-[[(6-choloro-1-oxopyridazin-3-yl) thio]methyl]-8-oxo-5-thia-1-azabicyclo [4.2.0]oct-2-ene-2-carboxylic acid, and 7β-[[D-[[(ethenylamino) carbonyl]amino]-2-thienylacetyl]amino]-3-[[(6-chloro-2-oxopyridazin-3-yl) thio]methyl]-8-oxo-5-thia-1-azabicyclo [4.2.0]oct-2-ene-2-carboxylic acid, respectively.

Similarly, by employing 3-[(acetyloxy) methyl]-7β-[[L- [[(ethenylamino) carbonyl]amino]-2-thienylacetyl]amino]-8-oxo-5-thia-1-azabicyclo [4.2.0 ]oct-2-ene-2-carboxylic acid, sodium salt in place of the D-isomer in examples 95 to 104, the corresponding final products in the L-isomer form are obtained. Additionally, the various 3-[(acetyloxy) methyl]-7α-methoxy or desmethoxy-7β-acylureido-cephalosporanic acid sodium salts shown in Col. I of examples 79 to 93 may be employed in the procedure of examples 95 to 104 to obtain other compounds within the scope of the invention.

EXAMPLE 105

7α-Methoxy-7β-[[D,L-[[(ethenylamino) carbonyl]amino]-2-thienylacetyl]amino]-3-[[(1-methyl-1H-tetrazol-5-yl) thio) methyl]-8-oxo-5-thia-1-azabicyclo[4.2.0]oct-2-ene-2-carboxylic acid a. [(Acetyloxy) methyl]-7α-methoxy-7β-[[D,L-[[[(4-methoxyphenyl) methoxy]carbonyl]amino]-2-thienylacetyl]amino]-8-oxo-5-thia-1-azabicyclo[4.2.0]oct-2-ene-2-carboxylic acid, diphenylmethyl ester D,L-2-[[[(4-Methoxyphenyl) methoxy]carbonyl]amino]-2-thiopheneacetic acid and 3-[(acetyloxy) methyl]-7α-methoxy-7β-amino-8-oxo-5-thia-1-azabicyclo [4.2.0]oct-2-ene-2-carboxylic acid, diphenylmethyl ester are reacted according to either of the procedures set forth in example 52(a) to yield the titled compound.

b. 3-[(Acetyloxy) methyl]-7α-methoxy-7β-[D,L-2-amino-2-(2-thienyl) acetamido]-8-oxo-5-thia-1-azabicyclo[4.2.0]oct-2-ene-2carboxylic acid, trifluoroacetic acid salt (1:1)

The diphenylmethyl ester product from part (a) is reacted with trifluoroacetic acid in the presence of anisole according to the procedure of example 1(e) to yield the titled compound.

c. 3-[(Acetyloxy)methyl]-7α-methoxyl-7β-[[D,L-[[(ethenylamino)carbonyl]amino]-2-thienylacetyl]amino]-8-oxo-5-thia-1-azabicyclo [4.2.0]oct-2-carboxylic acid The trifluoroacetic acid salt product from part (b) is treated with isocyanatoethene according to the procedure of example 51(d) to yield 3-[(acetyloxy) methyl]-7α-methoxy-7β-[[D,L-[[(ethenylamino) carbonyl]amino]-2-thienylacetyl]amino]-8-oxo-5-thia-1-azabicyclo[4.2.0]oct-2-carboxylic acid.

d. 7α-Methoxy-7β-[[D,L-[[(ethenylamino) carbonyl]amino]-2-thienylacetyl]amino]-3-[[(1-methyl-1H-tetrazol-5-yl) thio]methyl]-8-oxo-5-thia-1-azabicyclo[4.2.0]oct-2-ene-2-carboxylic acid The product from part (c) is dissolved in a mixture of acetone:water (1:1) with the aid of 5N sodium hydroxide. The pH is adjusted to 7.6–8.0 and 5mmol. of 1-methyl-1H-tetrazole-5-thiol is added. The pH is maintained at 7.8 by the addition of 5N sodium hydroxide. The reaction mixture is heated at 50° to 60° for several hours. After cooling and distilling off the acetone, the mixture is acidified to pH 2.5 by the addition of 2N hydrochloric acid while cooling with ice. The resulting precipitate is extracted with ethyl acetate to yield 7α-methoxy-7β-[[D,L-[[(ethenylamino) carbonyl]amino]-2-thienylacetyl]amino]- 3-[[(1-methyl-1H-tetrazol-5-yl) thio]methyl]-8-oxo-5-thia-1-azabicyclo[4.2.0]oct-2-ene-2-carboxylic acid.

EXAMPLE 106–124

Following the procedure of example 105 but employing the 3[(acetyloxy) methyl]-7α-methoxy or desmethoxy-7β-acylureido cephalosporanic acid shown below in Col. I and the heteromercaptan shown below in Col. II, one obtains the 3-heterothio compounds shown in Col. III.

I

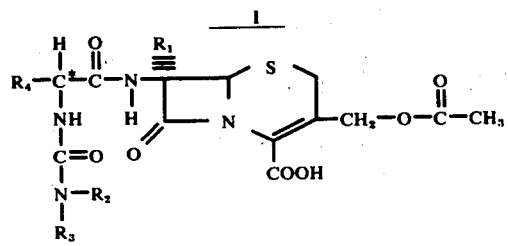

Col. II hetero-S—H col. III

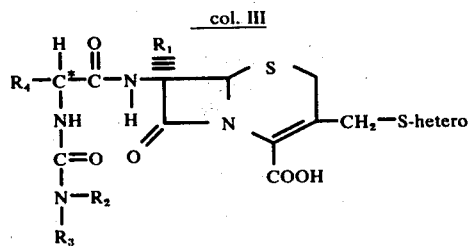

| Ex. | $R_1$ | $R_2$ | $R_3$ | $R_4$ | hetero |
|---|---|---|---|---|---|
| 106 | —H | —CH$_2$—CH=CH$_2$ | —H | thiophen-2-yl | 1-methyltetrazol-5-yl |
| 107 | —H | —CH=CH$_2$ | —CH$_3$ | thiophen-2-yl | 2-methyl-1,3,4-thiadiazol-5-yl |
| 108 | —OCH$_3$ | —CH$_2$—C≡CH | H | furan-2-yl | 2-methyl-1,3,4-thiadiazol-5-yl |
| 109 | —H | —CH(CH$_3$)—CH=CH$_2$ | —CH$_3$ | 5-chlorofuran-2-yl | 2-methyl-1,3,4-oxadiazol-5-yl |
| 110 | —H | —CH$_2$—C≡C—CH$_3$ | —H | phenyl | 1-methyltetrazol-5-yl |
| 111 | —OCH$_3$ | —CH(C$_2$H$_5$)—C≡CH | —CH$_3$ | phenyl | 1-methyltetrazol-5-yl |
| 112 | —H | —CH$_2$—CH=CH—CH$_3$ | —H | 4-hydroxyphenyl | 4-methylthiazol-2-yl |
| 113 | —OCH$_3$ | —CH(CH$_3$)—C≡CH | —C$_2$H$_5$ | phenyl | 1-methyltetrazol-5-yl |
| 114 | —H | —CH=CH$_2$ | —H | phenyl | 1-methyltetrazol-5-yl |
| 115 | —H | —CH$_2$—C≡CH | —CH$_3$ | thiophen-2-yl | 1-methyltetrazol-5-yl |
| 116 | —OCH$_3$ | —CH(C$_3$H$_7$)—CN=CH$_2$ | —C$_2$H$_5$ | cyclohexenyl | 1-methyltetrazol-5-yl |
| 117 | —H | —CH$_2$—CH=CH$_2$ | —H | cyclohexenyl | 2-methyl-1,3,4-thiadiazol-5-yl |
| 118 | —OCH$_3$ | —CH$_2$—CH=CH$_2$ | —CH$_2$—CH(CH$_3$)$_2$ | phenyl | 1-methyltetrazol-5-yl |
| 119 | —H | —CH=CH$_2$ | —C$_2$H$_5$ | phenyl | 1,3,4-thiadiazol-2-yl |
| 120 | —OCH$_3$ | —CH$_2$—C≡CH | —CH$_3$ | —C$_2$H$_5$ | 4-methylisothiazol-5-yl |

-continued

| Ex. | R₁ | R₂ | R₃ | R₄ | hetero |
|---|---|---|---|---|---|
| 121 | —H | —CH₂—C≡C—C₂H₅ | —CH₃ |  |  |
| 122 | —H | $\underset{\text{—CH—CH=CH}_2}{\overset{\text{CH}_3}{\mid}}$ | —H |  |  |
| 123 | —OCH₃ | —CH₂—CH=CH—CH₃ | —H |  |  |
| 124 | —OCH₃ | —CH₂—C≡CH | —CH₃ |  |  |

The 3-[(acetyloxy) methyl]-cephalosporanic acids of Col. I above may be in either the D- or L- isomer form or may be a mixture of the D- and L- isomers.

What is claimed is:
1. A compound of the formula:

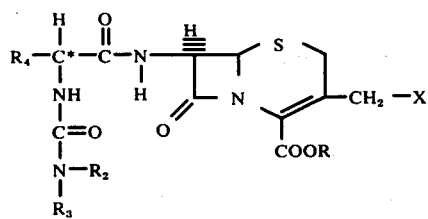

wherein R is hydrogen, lower alkyl, phenyl-lower alkyl, diphenyl-lower alkyl, tri(lower alkyl) silyl, trihaloethyl, an alkali metal ion, and alkaline earth metal ion, an alkaline earth metal ion, dibenzylamine, N,N-dibenzylethylenediamine, methylamine, triethylamino, N-ethylpiperidine or

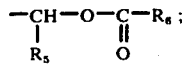

R₂ is lower alkenyl or lower alkinyl; R₃ is hydrogen or lower alkyl; R₄ is phenyl, phenyl-lower alkyl, substituted phenyl or phenyl-lower alkyl wherein said phenyl substituent is one or two members selected from the group consisting of halogen, lower alky of 1 to 4 carbons lower alkoxy of 1 to 4 carbons, and hydroxy, or a substituted or unsubstituted heterocyclic selected from the group consisting of 2-thienyl, 3-thienyl, 2-furyl, and 3-furyl wherein said heterocyclic substituent is attached at an available carbon atom and is halogen or lower alkyl of 1 to 4 carbons; R₅ is hydrogen or lower alkyl; R₆ is lower alkyl; and X is a heterothio group selected from the group consisting of

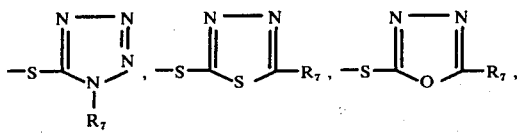

-continued

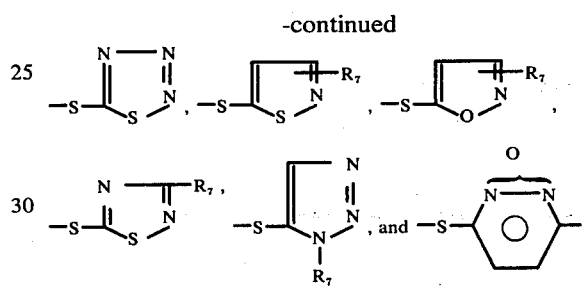

wherein R₇ is hydrogen or lower alkyl of 1 to 4 carbons and R₈ is hydrogen, lower alkyl of 1 4 carbons, methoxy, hydroxy, or halogen.

2. The compound of claim 1 wherein R is hydrogen straight or branched chain alkyl of 1 to 4 carbons, benzyl, phenethyl, diphenylmethyl, trimethylsilyl, 2,2,2-trichloroethyl, an alkali metal ion, and alkaline earth metal ion, dibenzylamine, N,N-dibenzylethylenediamine, methylamine, triethylamino, N-ethylpiperidine, or

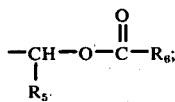

R₂ is lower alkenyl or lower alkinyl wherein said alkenyl or alkinyl is straight or branched chain of 2 to 8 carbons having one double or triple bond; R₃ is hydrogen or lower alkyl wherein lower alkyl is straight or branched chain of 1 to 8 carbons; R₄ is phenyl, benzyl, phenethyl, substituted phenyl, benzyl or phenethyl wherein said substituent is on the phenyl ring and is one or two members selected from the group consisting of chloro, bromo, methyl, ethyl, methoxy, ethoxy and hydroxy, or a substituted or unsubstituted heterocyclic selected from the group consisting of 2-thienyl, 3-thienyl, 2-furyl, and 3-furyl wherein said heterocyclic substituent is attached at an available carbon atom and is chloro, bromo, methyl, or ethyl, R₅ is hydrogen or straight or branched chain alkyl of 1 to 4 carbons; R₆ is straight or branched chain alkyl of 1 to 4 carbons; and X is a heterothio group selected from the group consisting of

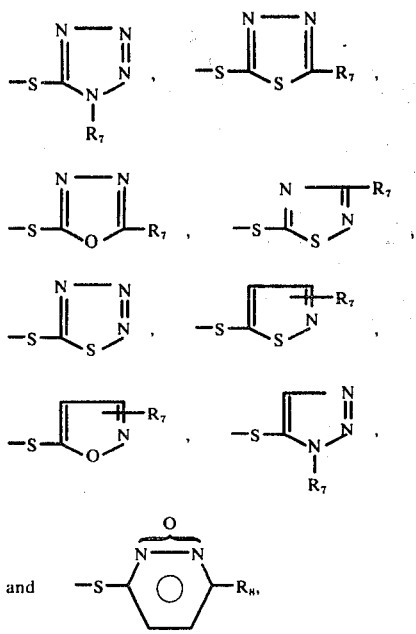

and 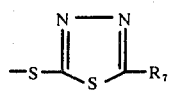

wherein R₇ is hydrogen, methyl, or ethyl and R₈ is hydrogen, methyl, ethyl, methoxy, hydroxy, or chlorine.

3. The compound of claim 2 wherein R is hydrogen, straight or branched chain alkyl of 1 to 4 carbons, benzyl phenethyl, diphenylmethyl, sodium or potassium; R₂ is lower alkenyl of lower alkinyl wherein said lower alkenyl or lower alkinyl is straight or branched chain alkyl of 1 to 4 carbons; R₃ is hydrogen or straight or branched chain alkyl of 1 to 4 carbons; R₄ is phenyl, benzyl, phenethyl, substituted phenyl, benzyl or phenethyl wherein said substituent is on the phenyl ring and is one or two members selected from the group consisting of chloro, bromo, methyl, ethyl, methoxy, ethoxy and hydroxy, or a substituted or unsubstituted heterocyclic selected from the group consisting of 2-thienyl, 3-thienyl, 2-furyl, and 3-furyl, wherein said heterocyclic substituent is attached at an available carbon atom and is chloro, bromo, methyl, or ethyl.

4. The compound of claim 3 wherein R is hydrogen, sodium or potassium; R₄ is 2-thienyl, 3-thienyl, phenyl or 4-hydroxyphenyl; and R₂ is lower alkenyl of 2 to 4 carbons.

5. The compound of claim 4 wherein X is

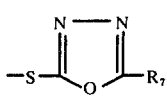

and R₇ is hydrogen, methyl, or ethyl.

6. The compound of claim 5 wherein R is hydrogen and R₇ is methyl.

7. The compound of claim 4 wherein X is

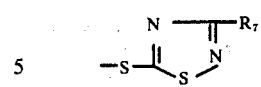

and R₇ is hydrogen, methyl, or ethyl.

8. The compound of claim 7 wherein R₇ is methyl and R is hydrogen.

9. The compound of claim 4 wherein X is

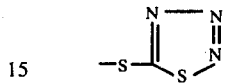

and R₇ is hydrogen, methyl, or ethyl.

10. The compound of claim 9 wherein R₇ is methyl and R is hydrogen.

11. The compound of claim 4 wherein X is

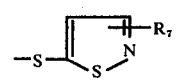

and R is hydrogen.

12. The compound of claim 4 wherein X is

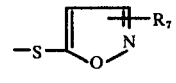

and R₇ is hydrogen, methyl, or ethyl.

13. The compound of claim 12 wherein R₇ is methyl and R is hydrogen.

14. The compound of claim 4 wherein X is

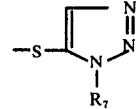

and R₇ is hydrogen, methyl, or ethyl.

15. The compound of claim 14 wherein R₇ is methyl and R is hydrogen.

16. The compound of claim 4 wherein X is

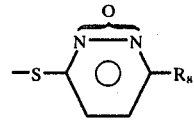

and R₇ is hydrogen, methyl, or ethyl.

17. The compound of claim 16 wherein R₇ is hydogen and R is hydrogen.

18. The compound of claim 4 wherein X is

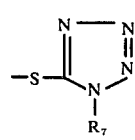

and R₈ is hydrogen, methyl, ethyl, methoxy, hydroxy, or chlorine.

19. The compound of claim 18 wherein R₈ is hydrogen and R is hydrogen.

20. The compound of claim 3 wherein X is and R₇ is hydrogen, methyl, or ethyl.

21. The compound of claim 20 wherein $R_7$ is methyl.

22. The compound of claim 21 wherein R is hydrogen, diphenylmethyl, sodium, or potassium; $R_4$ is 2-thienyl, 3-thienyl, phenyl or 4-hydroxyphenyl; and $R_2$ is lower alkenyl of 2 to 4 carbons.

23. The compound of claim 22 wherein $R_4$ is 2-thienyl.

24. The compound of claim 23 wherein $R_2$ is —CH$_2$—CH=CH$_2$.

25. The compound of claim 24 wherein R is diphenylmethyl.

26. The compound of claim 24 wherein R is hydrogen.

27. The compound of claim 24, 7β-[[D-[[(2-propenylamino) carbonyl]amino]-2-thienylacetyl]amino]-3-[[(1-methyl-1H-tetrazol-5-yl) thio]methyl]-8-oxo-5-thia-1-azabicyclo [4.2.0]oct-2-ene-2-carboxylic acid.

28. The compound of claim 24, 7β-[[L-[[(2-propenylamino) carbonyl]amino]-2-thienylacetyl]amino]-3[[(1-methyl-1H-tetrazol-5-yl) thio]methyl]-8-oxo-5-thia-1-azabicyclo [4.2.0]oct-2-ene-2-carboxylic acid.

29. The compound of claim 24 wherein R is sodium.

30. The compound of claim 29, 7β-[[D-[[(2-propenylamino) carbonyl]amino]-2-thienylacetyl]amino]-3-[[(1-methyl-1H-tetrazol-5-yl) thio]methyl]-8-oxo-5-thia-1-azabicyclo [4.2.0. [oct-2-ene-2-carboxylic acid, sodium salt.

31. The compound of claim 29, 7β-[[L-[[(2-propenylamino) carbonyl]amino]-2-thienylacetyl]amino]-3-[[(1methyl-1H-tetrazol-5-yl) thio]methyl]-8-oxo-5-thia-1-azabicyclo [4.2.0]oct-2-ene-2-carboxylic acid, sodium salt.

32. The compound of claim 22 wherein $R_2$ is —CH=CH$_2$.

33. The compound of claim 32 wherein R is hydrogen.

34. The compound of claim 32 wherein R is sodium.

35. The compound of claim 22 wherein $R_4$ is phenyl.

* * * * *

UNITED STATES PATENT AND TRADEMARK OFFICE
CERTIFICATE OF CORRECTION

PATENT NO. : 4,028,354
DATED : June 7, 1977
INVENTOR(S) : Hermann Breuer, Uwe D. Treuner It is certified that error appears in the above-identified patent and that said Letters Patent are hereby corrected as shown below:

Col. 1, formula Ia, insert circles around + and - signs;

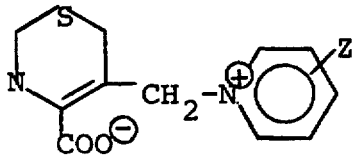

Col. 3, line 10 "chlorothienly" should read --chlorothienyl--.
Col. 3, line 12, "fromula" should read --formula--.
Col. 3, insert --or-- between formulas (III) and (IV).
Col. 4, line 11 "compounds" should read --compound--.
Col. 4, line 52, "fromula" should read --formula--.
Col. 5, formula XI, "metero" should read --hetero--.
Col. 8, line 17, "0°14°5°" should read -- 0-5° --.
Col. 8, line 38 "p-toluenesulfonic" should read--p-toluenesulfonic-
Col. 8, lines 49-50 "in vacuo" should read -- $\underline{in\ vacuo}$ --
Col. 8, line 50 "in vacuo" should read -- $\underline{in\ vacuo}$ --.
Col. 8, line 56, "chromotorgraphy" should read --chromatography--.
Col. 9, line 1 in Ex. 2, "carabonyl" should read -- carbonyl --.
Col. 9, line 50, [4.20] should read-[4.2.0]--.
Col. 9, line 60 "azabicyclo4.2.0]" should read --azabicyclo[4.2.0--
Col. 9, line 66, "caraboxylic" should read -- carboxylic --.
Col. 10, line 22, "7β- [[L" should read -- 7β-[[L --.
Col. 10, line 22, "carabonyl" should read -- carbonyl --.
Col. 10, line 25, "acid and its sodium salt" should read --acid, sodium salt. --.
Col. 10, line 22, "amino ]-3-" should read -- amino]-3- --.
Col. 17, line 37, delete "7".

UNITED STATES PATENT AND TRADEMARK OFFICE
CERTIFICATE OF CORRECTION

PATENT NO. : 4,028,354
DATED : June 7, 1977
INVENTOR(S) : Hermann Breuer, Uwe D. Treuner It is certified that error appears in the above-identified patent and that said Letters Patent are hereby corrected as shown below:

Col. 17, line 38, "β-[[D-" should read -- 7β-[[D- --.
Col. 17, line 52, "is dioxane" should read -- in dioxane --.
Col. 17, line 61, thiopheneacetic  acid; m.p." should read -- thiopheneacetic acid; m.p. --.
Col. 18, line 57, "[[81-" should read -- [[(1$\frac{}{D}$ --.
Col. 18, line 59 "[α]$_{20}$D" should read -- [α]$_{20}^D$ --.
Col. 20, line 6, "in vacuo" should read -- $\underline{in\ vacuo}$ --.
Col. 20, line 13, "in vacuo" should read -- $\underline{in\ vacuo}$ --.
Col. 24, "t-C$_4$H$_9$" should read --$\underline{t}$-C$_4$H$_9$-- (in line 57).
Col. 24, line 69, "t-C$_4$H$_9$" should read-$\underline{t}$-C$_4$H$_9$--.
Col. 26, line 67, "power" should read -- powder. --.
Col. 28, line 7, "7β[[L-" should read 7β-[[L- --.
Col. 27, formula Col. III, insert circle around + sign as follows:

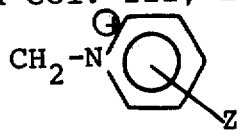

Col. 30, line 37, "[4.2.9]" should read --[4.2.0]--.
Col. 30, line 46, "6-t-butyl-" should read -- 6-$\underline{t}$-butyl- --.

UNITED STATES PATENT AND TRADEMARK OFFICE
CERTIFICATE OF CORRECTION

PATENT NO. : 4,028,354
DATED : June 7, 1977
INVENTOR(S) : Hermann Breuer, Uwe D. Treuner It is certified that error appears in the above-identified patent and that said Letters Patent are hereby corrected as shown below:

Col. 30, line 59, "lazabicyclo" should read -- 1-azabicyclo --.
Col. 30, line 66, "[[(6-t-butyl" should read -- [[(6-t-butyl --.
Col. 31, line 6, "(6-hydroxyl-1" should read -- (6-hydroxy-1 --.
Col. 31, line 45, "a. [(Acetyloxy)" should read -- a. 3-[(Acetyloxy)
Col. 31, line 61, "2carboxylic" should read -- 2-carboxylic --.
Col. 32, line 4, "oct-2-car" should read -- oct-2-ene-car --.
Col. 32, line 11 "oct-2-carboxylic" should read -- oct-2-ene-2-ene-carboxylic --.
Col. 35, line 53, "alky" should read -- alkyl --.
Col. 36, line 36, "1 4 carbons" should read -- 1 to 4 carbons --.
Col. 9, line 51, "(2-propenlyamino)" should read --(2-propenylamino)

Signed and Sealed this

Fourth Day of December 1979

[SEAL]

Attest:

SIDNEY A. DIAMOND

Attesting Officer

Commissioner of Patents and Trademarks